US007189541B2

(12) United States Patent  
Donovan

(10) Patent No.: US 7,189,541 B2  
(45) Date of Patent: Mar. 13, 2007

(54) BOTULINUM TOXIN PRODUCTION METHOD

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/296,015

(22) Filed: Dec. 7, 2005

(65) Prior Publication Data

US 2006/0228777 A1    Oct. 12, 2006

Related U.S. Application Data

(62) Division of application No. 10/672,876, filed on Sep. 25, 2003, now Pat. No. 7,148,041.

(51) Int. Cl.  
C12P 21/04      (2006.01)  
C12N 1/00       (2006.01)  
C12N 1/20       (2006.01)

(52) U.S. Cl. ............... 435/71.1; 435/252.7; 435/253.6; 435/842; 424/236.1; 424/239.1

(58) Field of Classification Search ............... 435/71.1, 435/252.7, 253.6, 842; 424/842, 236.1, 239.1  
See application file for complete search history.

(56) References Cited

U.S. PATENT DOCUMENTS

| | | | |
|---|---|---|---|
| 6,558,926 B1 | 5/2003 | Demain et al. | |
| 2003/0118598 A1 | 6/2003 | Hunt et al. | |

FOREIGN PATENT DOCUMENTS

| | | |
|---|---|---|
| WO | WO 94/09115 | 10/1993 |
| WO | WO 98/54296 | 5/1998 |
| WO | WO 01/05997 A2 | 7/2000 |
| WO | WO 01/05997 A3 | 7/2000 |
| WO | WO 01-36655 | 10/2000 |
| WO | WO 01/58472 | 2/2001 |

OTHER PUBLICATIONS

Naumann, M., et al., Botulinum toxin type A in the treatment of focal, axillary and palmar hyperhidrosis and other hyperhidrotic conditions, Euro. J. Neurology 1999:6(Suppl 4):S111-S115.
Porfirio, Z., et al., Specific peptides of casein pancreatic digestion enhance the production of tetanus toxin, J. of Applied Microbiology, 1997 83:678-684.
Ragona, Rosario Marchese, et al., Management of Parotid Sialocele with botulinum toxin, The Laryngoscope, 109:Aug. 1999:pp. 1344-1346.
Siegel, L.S., Fermentaton kinetics of botulinum toxin production (types A, B and E), Biomedical aspects of botulism, New York: Academic Press 1981:pp. 121-128.
Schantz, E.J., et al., Preparation and characterization of botulinum toxin type A for human treatment, Jankovic J, ed.; Neurological Disease and Therapy. Therapy withBotulinum Toxin, 1994;25:pp. 41-49.
Schantz, E.J., et al., Properties and use of botulinum toxin and other miorobial neurotoxins in medicine, Microbiological Reviews, Mar. 1992, p. 80-99.
Schiefer-Ullrich, H., et al., Comparative studies on physiology and taxonomy of obligatory purinolytic clostridia, Arch Microbial, 1984, 138:345-353.
Whitmer, M.E., et al., Development of improved defined media for clostridium botulinum serotypes A, B and E, Applied and Environmental Microbiology, Mar. 1988, vol. 54, No. 3, p. 753-759.
Heenan, C. N., et al., Lehensm.-Wiss. U.-Technol, 35 (2002), pp. 171-176.
Miwa, Norinaga, et al., International Journal of Food Microbiology, 49 (1999), pp. 103-106.
Mueller, J. H., et al., J. Bacteriology, Mar. 1954, 67(3), pp. 271-277.
Whitmer, M. E., et al., Applid and Environmental Microbiology, Mar. 1988, 54(3), pp. 753-759.
Oxoid—Product CM0149—product description, pp. 1-2.
Coligan, et al., Current protocols in protein science, Front Matter, Aug. 2003.
Lungdahl, L.G., et al., Working with anaerobic bacteria, Manual of Industrial Microbiology and Biotechnology, Chp. 8, 1986, pp. 84-96.
Mueller, J.H., et al., Variable factors influencing the product of tetanus toxin, J. Bacteriol, 1954; 67:271-7.
Ozutsumi, K., et al., Rapid, simplified method for production and purification of tetanus toxin, Applied and Environmental Microbiology, Apr. 1985, vol. 49, No. 4, pp. 939-943.
Chp. 1, pp. 1-88, Strategies of Protein Purification and Characterization, Current Protocols in Protein Science, Front Matter, (2003) John E. Coligan, et al., Ed, Chp. 21, pp. 1-282.
Chp. 21, pp. 1-282, Peptidases, Current Protocols in Protein Science, Front Matter, (2003) John E. Coligan, et al., Ed.
Bonventre, P.F., et al., Physiology of toxin production by clostridium botulinum types A and B, College of Medicine, vol. 7, pp. 372-374.
Chen, F., et al., Biophysical characterization of the stability of the 150-kilodalton botulinum toxin, the nontoxic component and the 900-kilodalton botulinum toxin complex species, Infect Immun Jun. 1998;66(6):2420-2425.
Holdeman, L., et al., A study of the nutritional requirements and toxin production of clostridium botulinum type F, Canadian Journal of Microbiology, vol. 11, (1965), pp. 1009-1019.
Johnson, E., et al., Clostridium botulinum and its neurotoxins: a metabolic and cellular perspective, Toxicon 39 (2001) 1703-1722.
Karasawa, T., et al., A defined growth medium for clostridium difficle, Microbiology (1995), 141, 371-375.
Kohl, A., et al., Comparison of the effect of botulinum toxin A (BOTOX®) with the highly-purified neurotoxin (NT201) n the extensor digitorum brevis muscle test, Mov Disord, 2000;15(Suppl 3):165.
Lewis, K.H., et al., Practical media and control measures for highly toxic cultures of clostridium botulinum type A, Production of Botulinum Toxin, pp. 213-230, 1947.
Li, Y., et al., Expression and characterization of the heavy chain of tetanus toxin: reconstitution of the fully-recombinant dichain protein in active form, J Biochem (Tokyo) Jun. 1999;125(6):1200-1208.

Primary Examiner—Chih-Min Kam  
(74) Attorney, Agent, or Firm—Stephen Donovan

(57) ABSTRACT

Media and processes for the fermentation of *Clostridium botulinum* and obtaining a *botulinum* toxin for use in formulating *botulinum* toxin pharmaceutical compositions. The growth media can contain significantly reduced levels of meat or dairy by-products using non-animal based products to replace the animal-derived products. Preferably, the media used are substantially free of animal derived products.

9 Claims, No Drawings

BOTULINUM TOXIN PRODUCTION METHOD

CROSS REFERENCE

This application is a divisional of U.S. application Ser. No. 10/672,876, filed Sep. 25, 2003, now U.S. Pat. No. 7,148,041.

BACKGROUND

The present invention relates to a medium and to a process for obtaining biologically active *botulinum* toxin. In particular, the present invention relates to substantially animal product free, media, culture and anaerobic fermentation processes of an organism, such as a *Clostridium botulinum* bacterium, for obtaining abundant, biologically active *botulinum* toxin.

A pharmaceutical composition suitable for administration to a human or animal for a therapeutic) diagnostic, research or cosmetic purpose can comprise an active ingredient. The pharmaceutical composition can also include one or more excipients, buffers, carriers, stabilizers, preservatives and/or bulking agents. The active ingredient in a pharmaceutical composition can be a biologic such as a *botulinum* toxin. The *botulinum* toxin can be obtained through a culturing, fermentation and compounding process which makes use of one or more animal derived products (such an a meat broth culture medium, and a blood fraction or blood derivative excipient). Administration to a patient of a pharmaceutical composition wherein the active ingredient biologic is obtained through a process which makes use of animal derived products can subject the patient to a potential risk of receiving various pathogens or infectious agents. For example, prions may be present in a pharmaceutical composition. A prion is a proteinaceous infectious particle which is hypothesized to arise as an abnormal conformational isoform from the same nucleic acid sequence which makes the normal protein. It has been further hypothesized that infectivity resides in a "recruitment reaction" of the normal protein. It has been further hypothesized that infectivity resides in a "recruitment reaction" of the normal isoform protein to the prion protein isoform at a post translational level. Apparently the normal endogenous cellular protein is induced to misfold into a pathogenic prion conformation.

Creutzfeldt-Jacob disease is a rare neurodegenerative disorder of human transmissible spongiform encephalopathy where the transmissible agent is apparently an abnormal isoform of a prion protein. An individual with Creutzfeldt-Jacob disease can deteriorate from apparent perfect health to akinetic mutism within six months. Thus, a potential risk may exist of acquiring a prion mediated disease, such as Creutzfeldt-Jacob disease, from the administration of a pharmaceutical composition which contains a biologic, such as a *botulinum* toxin, obtained using animal derived products.

Botulinum Toxin

The genus *Clostridium* has more than one hundred and twenty seven species, grouped by morphology and function. The anaerobic, gram positive bacterium *Clostridium botulinum* produces a potent polypeptide neurotoxin, *botulinum* toxin, which causes a neuroparalytic illness in humans and animals known as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

Botulinum toxin type A is the most lethal natural biological agent known to man. About 50 picograms of *botulinum* toxin (purified neurotoxin complex) type A is a $LD_{50}$ in mice. On a molar basis, *botulinum* toxin type A is 1.8 billion times more lethal than diphtheria, 600 million times more lethal than sodium cyanide, 30 million times more lethal than cobrotoxin and 12 million times more lethal than cholera. Singh, Critical Aspects of Bacterial Protein Toxins, pages 63–84 (chapter 4) of Natural Toxins II, edited by B. R. Singh et al., Plenum Press, New York (1976) (where the stated $LD_{50}$ of *botulinum* toxin type A of 0.3 ng equals 1 U is corrected for the fact that about 0.05 ng of BOTOX® equals 1 unit). BOTOX® is the trademark of a *botulinum* toxin type A purified neurotoxin complex available commercially from Allergan, Inc., of Irvine, Calif. One unit (U) of *botulinum* toxin is defined as the $LD_{50}$ upon intraperitoneal injection into female Swiss Webster mice weighing 18–20 grams each. In other words, one unit of *botulinum* toxin is the amount of *botulinum* toxin that kills 50% of a group of female Swiss Webster mice. Seven generally immunologically distinct *botulinum* neurotoxins have been characterized, these being respectively *botulinum* neurotoxin serotypes A, B, $C_1$, D, E, F, and G, each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. The *botulinum* toxins apparently bind with high affinity to cholinergic motor neurons, are translocated into the neuron and block the presynaptic release of acetylcholine.

Botulinum toxins have been used in clinical settings for the treatment of e.g. neuromuscular disorders characterized by hyperactive skeletal muscles. Botulinum toxin type A has been approved by the U.S. Food and Drug Administration for the treatment of essential blepharospasm, strabismus and hemifacial spasm in patients over the age of twelve, for the treatment of cervical dystonia and for the treatment of glabellar line (facial) wrinkles. The FDA has also approved a *botulinum* toxin type B for the treatment of cervical dystonia. Clinical effects of peripheral injection (i.e. intramuscular or subcutaneous) *botulinum* toxin type A are usually seen within one week of injection, and often within a few hours after injection. The typical duration of symptomatic relief (i.e. flaccid muscle paralysis) from a single intramuscular injection of *botulinum* toxin type A can be about three months to about six months.

Although all the *botulinum* toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to *botulinum* toxin type A. Botulinum toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of *botulinum* toxin and for *botulinum* toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to is possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and *botulinum* toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Botulinum neurotoxin, *botulinum* toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemagglutinin protein and a non-toxin and non-toxic non-hemagglutinin protein. These two non-toxin proteins (which along with the *botulinum* toxin molecule can comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex. The toxin complexes can be dissociated into toxin protein and hemagglutinin proteins by treating the complex with red blood cells at pH 7.3. The toxin protein has a marked instability upon removal of the hemagglutinin protein.

All the *botulinum* toxin serotypes are made by *Clostridium botulinum* bacteria as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

High quality crystalline *botulinum* toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline *botulinum* toxin type A, asset forth in Schantz, E. J., et al, *Properties and use of Botulinum toxin and Other Microbial Neurotoxins in Medicine*, Microbiol Rev. 56: 80–99 (1992). Generally, the *botulinum* toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline *botulinum* toxin type A complex with a specific potency of $3 \times 10^7$ $LD_{50}$ U/mg or greater. This known process can also be used, upon separation out of the non-toxin proteins, to obtain pure *botulinum* toxins, such as for example: purified *botulinum* toxin type A with an approximately 150 kD molecular weight with a specific potency of $1-2 \times 10^8$ $LD_{50}$ U/mg or greater; purified *botulinum* toxin type B with an approximately 156 kD molecular weight with a specific potency of $1-2 \times 10^8$ $LD_{50}$ U/mg or greater, and; purified *botulinum* toxin type F with an approximately 155 kD molecular weight with a specific potency of $1-2 \times 10^7$ $LD_{50}$ U/mg or greater.

Botulinum toxins (the 150 kilodalton molecule) and *botulinum* toxin complexes (300 kDa to 900 kDa) can be obtained from, for example, List Biological Laboratories, Inc., Campbell, Calif.; the Centre for Applied. Microbiology and Research, Porton Down, U.K.; Wako (Osaka, Japan), as well as from Sigma Chemicals of St Louis, Mo. Commercially available *botulinum* toxin containing pharmaceutical compositions include Botox® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising *botulinum* toxin type B, human serum albumin, sodium succinate, and sodium chloride at about pH 5.6, available from Elan Corporation, Dublin, Ireland).

The success of *botulinum* toxin type A to treat a variety of clinical conditions has led to interest in other *botulinum* toxin serotypes. Thus, at least *botulinum* toxins types, A, B, E and F have been used clinically in humans. Additionally, pure (approx 150 kDa) *botulinum* toxin has been used to treat humans. See e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165. Hence, a pharmaceutical composition can be prepared using a pure (approx 150 kDa) *botulinum* toxin.

The type A *botulinum* toxin is know to be soluble in dilute aqueous solutions at pH 4–6.8. At pH above about 7 the stabilizing nontoxic no proteins dissociate from the neurotoxin, resulting in a gradual loss of toxicity, particularly as the pH and temperature rise. Schantz E. J., et al *Preparation and characterization of botulinum toxin type A for human treatment* (in particular pages 44–45), being chapter 3 of Jankovic, J., et al, *Therapy with Botulinum Toxin*, Marcel Dekker, Inc (1994).

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

It has been reported that a *botulinum* toxin has been used in various clinical settings, including as follows:

(1) about 75–125 units of BOTOX® per intramuscular injection (multiple muscles) to treat cervical dystonia;
(2) 5–10 units of BOTOX® per intramuscular injection to treat glabellar lines (brow furrows) (5 units injected intramuscularly into the procerus muscle and 10 units injected intramuscularly into each corrugator supercilii muscle);
(3) about 30–80 units of BOTOX® to treat constipation by intrasphincter injection of the puborectalis muscle;
(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extrabcular muscles have been injected intramuscularly with between about 1–5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
    (a) flexor digitorum profundus: 7.5 U to 30 U
    (b) flexor digitorum sublimus: 7.5 U to 30 U
    (c) flexor carpi ulnaris: 10 U to 40 U
    (d) flexor carpi radialis: 15 U to 60 U
    (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that *botulinum* toxin type A can have an efficacy for up to 12 months (*European J. Neurology* 6 (Supp 4): S111–S1150:1999), and in some circumstances for as long as 27 months. The *Laryngoscope* 109:1344–1346: 1999. However, the usual duration of an intramuscular injection of Botox® is typically about 3 to 4 months.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, human serum albumin, and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. For sterility reasons, BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C.

In general, four physiologic groups of *C. botulinum* are recognized (I, II, III, and IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce *botulinum* neurotoxins.

The physiologic groups of *Clostridium botulinum* types are listed in Table I.

What is needed therefore are media and processes which are free or substantially free of animal products, such as animal derived proteins, for obtaining or producing biologically active *botulinum* toxin.

SUMMARY

The present invention meet this need and provides media and processes which are free or substantially free of animal products, such as animal derived proteins, for obtaining or producing a biologically active *botulinum* toxin. The *botulinum* toxin obtained can be used to make *botulinum* toxin active ingredient pharmaceutical compositions.

Definitions

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intracranial, intraperitoneal (i.p.) administration,

TABLE I

Physiologic Groups of *Clostridium botulinum*

| Group | Toxin Sero-Type | Biochemistry | Milk Digest | Glucose Fermentation | Lipase | Phages & Plasmids | Phenotypically Related *Clostridium* (nontoxigenic) |
|---|---|---|---|---|---|---|---|
| I | A, B, F | proteolytic saccharolytic | + | + | + | + | *C. sporogenes* |
| II | B, E, F | nonproteolytic saccharolytic psychotrophic | − | + | + | + | |
| III | C, D | nonproteolytic saccharolytic | ± | + | + | + | *C. novyi* |
| IV | G | proteolytic nonsaccharolytic | + | − | − | − | *C. subterminale* |

These toxin types may be produced by selection from the appropriate physiologic group of *Clostridium botulinum* organisms. The organisms designated as Group I are usually referred to as proteolytic and produce *botulinum* toxins of types A, B and F. The organisms designated as Group II are saccharolytic and produce *botulinum* toxins of types B, E and F. The organisms designated as Group III produce only *botulinum* toxin types C and D and are distinguished from organisms of Groups I and II by the production of significant amounts of propionic acid. Group IV organisms produce only neurotoxin of type G.

It is known to obtain a tetanus toxin using specific media substantially free of animal products. See e.g. U.S. Pat. No. 6,558,926. But notably, even the "animal product free" media disclosed by this patent uses Bacto-peptone, a meat digest). Significantly, production of tetanus toxin by clostridium tetani vs. production of a *botulinum* toxin by a *clostridium botulinum* bacterium entails different growth, media and fermentation parameters and considerations. See e.g. Johnson, E. A., et al., *Clostridium botulinum and its neurotoxins: a metabolic and cellular perspective*, Toxicon 39 (2001), 1703–1722.

topical (transdermal) and implantation (i.e. of a slow-release device such as polymeric implant or miniosmotic pump) routes of administration.

"Animal product free" or "substantially animal product free" encompasses, respectively, "animal protein free" or "substantially animal protein free" and means the absence or substantial absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal product free medium or process or a substantially animal product free medium or process within the scope of my invention can include a *botulinum* toxin or a *Clostridial botulinum* bacterium. For example, an animal product free process or a substantially animal product free process means a process which is either substantially free or essentially free or entirely free of animal derived proteins, such as immunoglobulins, meat digest, meat by products and milk or dairy products or digests. Thus, an example of an animal product free process is a process (such as a bacterial culturing or bacterial fermentation process) which excludes meat and dairy products or meat or dairy by products.

"Botulinum toxin" means a neurotoxin produced by *Clostridium botulinum*, as well as a *botulinum* toxin (or the light chain or the heavy chain thereof) made recombinantly by a non-*Clostridial* species. The phrase "*botulinum* toxin", as used herein, encompasses the *botulinum* toxin serotypes A, B, C, D, A, F and G. Botulinum toxin, as used herein, also encompasses both a *botulinum* toxin complex (i.e. the 300, 600 and 900 kDa complexes) as well as the purified *botulinum* toxin (i.e. about 150 kDa). "Purified *botulinum* toxin" is defined as a botulinum toxin that is isolated, or substantially isolated, from other proteins, including proteins that form a *botulinum* toxin complex. A purified *botulinum* toxin may be greater than 95% pure, and preferably is greater than 99% pure. The *botulinum* $C_2$ and $C_3$ cytotoxins, not being neurotoxins, are excluded from the scope of the present invention.

"*Clostridial* neurotoxin" means a neurotoxin produced from, or native to, a *Clostridial* bacterium, such as *Clostridium botulinum, Clostridium butyricum* or *Clostridium beratti*, as well as a *Clostridial* neurotoxin made recombinantly by a non-*Clostridial* species.

"Entirely free" (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Immobilizing" means a step that prevents a subject from moving one or more body parts. If a sufficient number of body parts are immobilized, the subject will accordingly be immobilized. Thus, "immobilizing" encompasses the immobilization of a body part, such as a limb, and/or the complete immobilization of a subject.

"Modified *botulinum* toxin" means a *botulinum* toxin that has had at least one of its amino acids deleted, modified, or replaced, as compared to a native *botulinum* toxin. Additionally, the modified *botulinum* toxin can be a recombinantly produced neurotoxin, or a derivative or fragment of a recombinantly made neurotoxin. A modified *botulinum* toxin retains at least one biological activity of the native *botulinum* toxin, such as, the ability to bind to a *botulinum* toxin receptor, or the ability to inhibit neurotransmitter release from a neuron. One example of a modified *botulinum* toxin is a *botulinum* toxin that has a light chain from one *botulinum* toxin serotype (such as serotype A), and a heavy chain from a different *botulinum* toxin serotype (such as serotype B). Another example of a modified *botulinum* toxin is a *botulinum* toxin coupled to a neurotransmitter, such as substance P.

"Patient" means a human or non-human subject receiving medical or veterinary care. Accordingly, as disclosed herein, the compositions may be used in treating any animal, such as mammals.

"Pharmaceutical composition" means a formulation in which an active ingredient can be a *botulinum* toxin. The word "formulation" means that there is at least one additional ingredient in the pharmaceutical composition besides a neurotoxin active ingredient. A pharmaceutical composition is therefore a formulation which is suitable for diagnostic or therapeutic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The active ingredient can be one of the *botulinum* toxin serotypes A, B, $C_1$, D, E, F or G or a *botulinum* toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use. Methods for formulating a *botulinum* toxin active ingredient pharmaceutical composition are disclosed in U.S. patent publication 2003 0118598 A1.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

The present invention provides media which comprise at least reduced levels of animal or dairy byproducts and are preferably substantially free of animal or dairy byproducts. "Animal or dairy byproducts;" means any compound or combination of compounds which was produced in or by an animal (excluding a bacterial) cell, whether in vivo or in vitro. Preferred non-animal sources of media ingredients such as proteins, amino acids; and nitrogen, include vegetables, microbes (such as yeast) and synthetic compounds.

My invention also provides methods for obtaining *botulinum* toxin using at least one medium that is substantially free of animal or dairy byproducts. For example, the *botulinum* toxin can be obtained by culturing *Clostridium botulinum* in a fermentation medium which is substantially free of animal products.

My invention also encompasses,; a *botulinum* toxin obtained by culturing *Clostridium botulinum* in a fermentation medium substantially free of animal products and which comprises vegetable derived products. Additionally, a *botulinum* toxin can be obtained by culturing *Clostridium botulinum* in a fermentation medium which is substantially free of animal products and which comprises some soy-based products.

In another preferred embodiment, a *botulinum* toxin can be obtained by culturing *Clostridium botulinum* in a fermentation medium substantially free of animal products and containing hydrolyzed soy, as a substitute for animal-derived products. Preferably, growth in a fermentation medium proceeds until at least cell lysis occurs. The source of *Clostridium botulinum* used for inoculation of the fermentation medium may be obtained from a seed medium containing *Clostridium botulinum*. Preferably, *Clostridium botulinum* grown in a seed medium and used as an inoculant for a fermentation medium has not undergone cell lysis. The source of *Clostridium botulinum* used for inoculation of the seed medium may be obtained from a lyophilized culture. *Clostridium botulinum* may be lyophilized as a culture in animal milk or soy milk. Preferably the *Clostridium botulinum* is lyophilized as a culture in soy milk.

The present invention also provides a composition comprising a medium substantially free of animal-derived products for culturing *Clostridium botulinum*.

In one embodiment, the composition comprises a medium substantially free of animal-derived products while containing at least one product derived from a non-animal source, and also comprising a *Clostridium botulinum*.

In another embodiment, the composition comprises a medium substantially free of animal-derived products while containing at least one product derived from a vegetable, and also comprising a *Clostridium botulinum*. A final embodiment of my invention can be a composition which comprises a medium which is substantially free of animal-derived products while containing at least one product derived from soybeans, and also comprising a *Clostridium botulinum*.

DESCRIPTION

The present invention is based upon the discovery of media and processes which are free or substantially free of an animal product or an animal byproduct useful for culture and fermentation of an organism (such as a *Clostridium botulinum* bacterium) capable of producing biologically active *botulinum* toxin. The *botulinum* toxin obtained can be used for making *botulinum* toxin active ingredient pharmaceutical compositions. Thus, growth media are disclosed herein which have significantly reduced levels of meat or dairy by-products and preferred media embodiments are substantially free of such animal products.

The present invention encompasses my surprising finding that animal-based products are not required in media for growth of *Clostridium botulinum*, and particularly that vegetable-based products can replace animal-based products typically employed in such media for the growth of *Clostridium botulinum*.

Media that are in current use for growth and fermentation of bacteria usually comprise one or more animal derived ingredients. In accordance with my invention, preferred media for growth of *Clostridium botulinum* contain anima derived ingredients which comprise no more than about five to about ten percent of the total weight of the media. More preferably, media within the scope of my invention comprise no more than about one to less than about five percent of the total weight of the media of anima-derived products. Most preferably, all media and cultures used for the growth of *Clostridium botulinum* for the production of *botulinum* toxin are completely free of animal derived products. These media include but are not limited to media for small and large scale fermentation of *Clostridium botulinum*, media for growth of cultures of *Clostridium botulinum* used to inoculate the seed (first) media and fermentation (second) media, as well as and media used for long-term storage of cultures of *Clostridium botulinum* (e.g. stock cultures).

In certain preferred embodiments of my invention, the media for the growth of *Clostridium botulinum* and production of *botulinum* toxin can comprise soy based products to replace animal derived products. Alternately, instead of a soy based product there can be used debittered seed of Lupinus campestris. It is known the protein content of L. campestris seed is very similar to that of soybean. Preferably, these media include soybean or of L. campestris derived products that are hydrolyzed and that are soluble in water. However, insoluble soy or of L. campestris products can also be used in the present invention to replace animal products. Common animal derived products which can be substituted by soy or of L. campestris products include beef heart infusion (BHI), animal derived peptone products, such as. Bacto-peptone, hydrolyzed caseins, and dairy by-products such as animal milk.

Preferably media containing soy-based or of L. campestris based products for the growth of *Clostridium botulinum* are similar to commonly used growth media containing animal derived products except that Substantially all animal-derived products are replaced with vegetable-derived products. For example, soy based fermentation media can comprise a soy based product, a source of carbon such as glucose, salts such as NaCl and KCl, phosphate-containing ingredients such as $Na_2HPO_4$, $KH_2PO_4$, divalent cations such as iron and magnesium, iron powder, and amino acids such as L-cysteine and L-tyrosine. Media used to grow cultures of *Clostridium botulinum* for inoculation (i.e. the seed or first medium) of the fermentation (second) media preferably contain at least a soy based product, a source of salt such as NaCl, and a carbon source such as glucose.

The present invention provides a method for the growth of *Clostridium botulinum* that maximizes the production of a *botulinum* toxin using media that are substantially free of animal-derived products. Growth for production of *Clostridium botulinum* and *botulinum* toxin can take place by fermentation in media containing soy by-products that replace ingredients derived from animal by-products. The inoculant for the fermentation medium can be derived from a smaller scaled growth medium (a seed medium). Depending on the size and volume of the fermentation step, the number of successive growths in seed media to increase the biomass of the culture can vary. To grow a suitable amount, of *Clostridium botulinum* for inoculating the fermentation medium, one step or multiple steps involving growth in a seed medium can be performed. For a method of growing *Clostridium botulinum* that is free of animal derived products, it is preferable that growth of *Clostridium botulinum* originates from a culture stored in non animal derived media. The stored culture, preferably lyophilized, is produced by growth in media containing proteins derived from soy and lacking animal by-products. Growth of *Clostridium botulinum* in a fermentation medium can take place by inoculation directly from a stored, lyophilized culture.

In a preferred embodiment of the present invention, growth of *Clostridium botulinum* proceeds in two phases-seed growth and fermentation. Both of these phases are carried out in anaerobic environments. The seed growth phase is generally used to "scale-up" the quantity of the microorganism from a stored culture. The purpose of the seed growth phase) is to increase the quantity of the microorganism available for fermentation. In addition, the seed growth phase allows relatively dormant microbes in stored cultures to rejuvenate and grow into actively growing cultures. Furthermore, the volume and quantity of viable microorganisms used to inoculate the fermentation culture can be controlled more accurately from an actively growing culture than from a stored culture. Thus, growth of a seed culture for inoculation of the fermentation medium is preferred. In addition, any number of consecutive steps involving growth in seed media to scale-up the quantity of *Clostridium botulinum* for inoculation of the fermentation medium can be used. It is noted that growth of *Clostridium botulinum* in the fermentation phase can proceed directly from the stored culture by direct inoculation.

In the fermentation phase, a portion of a seed medium or all of a seed medium containing *Clostridium botulinum* from the seed growth is used to inoculate a fermentation medium. Preferably, approximately 2–4% of a seed medium having *Clostridium botulinum* from the seed growth phase is used to inoculate the fermentation medium. Fermentation is used to produce the maximum amount of microbe in a large-scale anaerobic environment (Ljungdahl et al., *Manual of industrial microbiology and biotechnology* (1986), edited by Demain et al, American Society for Microbiology, Washington, D.C. page. 84).

A *botulinum* toxin can be isolated and purified using methods of protein purification well known to those of ordinary skill in the protein purification art (Coligan et al. *Current Protocols in Protein Science*, Wiley & Sons; Ozutsumi et al. Appl. Environ. Microbiol. 49; 939–943:1985.

For production of *botulinum* toxin, cultures of *Clostridium botulinum* 30 can be grown in a seed medium for inoculation of the fermentation medium. The number of successive steps involving growth in a seed medium can vary depending on the scale of the production of *botulinum* toxin in the fermentation phase. However, as previously discussed, growth in the fermentation phase may proceed directly from inoculation from a stored culture. Animal-based seed media generally are comprised of BHI, bactopeptone, NaCl, and glucose for growth of *Clostridium botulinum*. As previously discussed, alternative seed media may be prepared in accordance with the present invention in which animal-based components are substituted with non-animal-based components. For example but without limitation, soy-based products can substitute for BHI and bactopeptone in the seed medium for growth of *Clostridium botulinum* and production of Botulinum Toxin. Preferably, the soy-based product is soluble in water and comprises hydrolyzed soy, although cultures of *Clostridium botulinum* can grow in media containing insoluble soy. However, levels of growth and subsequent toxin production are greater in media derived from soluble soy products.

Any source of soy-based products may be used in accordance with the present invention. Preferably, the soy is hydrolyzed soy. Sources of hydrolyzed soy are available from a variety of commercial vendors. These include but are not limited to Hy-Soy (Quest International), Soy peptone (Gibco) Bac-soytone (Difco), AMISOY (Quest), NZ soy, (Quest), NZ soy BL4, NZ soy BL7, SE50M (DMV International Nutritionals, Fraser, N.Y.), and SE50MK (DMV). Most preferably, the source of hydrolyzed soy is Hy-Soy or SE50MK. Other potential sources of hydrolyzed soy are known.

Concentrations of Hy-Soy in the seed medium in accordance with the present invention range between 25–200 g/L. Preferably, the concentration of Hy-Soy in the seed medium ranges between 50–150 g/L. Most preferably the concentration of Hy-Soy in the seed medium is approximately 100 g/L. In addition, the concentration of NaCl ranges between 0.1–2.0 g/L. Preferably the concentration of NaCl ranges between 0.2–1.0 g/L. Most preferably, the concentration of NaCl in the seed medium is approximately 0.5 g/L. The concentration of glucose ranges between 0.1 g/L and 5.0 g/L. Preferably, the concentration of glucose ranges between 0.5–2.0 g/L. Most preferably, the concentration of glucose in the seed medium is approximately 1.0 g/L. It is also preferred but not necessary for the present invention that the glucose is sterilized by autoclaving together with the other components of the seed medium. The preferred pH level of the seed medium prior to growth ranges between 7.5–8.5. Most preferably, the pH of the seed medium prior to growth of *Clostridium botulinum* is approximately 8.1.

Growth of *Clostridium botulinum* in the seed medium may proceed in one or more stages. Preferably, growth in the seed medium proceeds in two stages. In stage one, a culture of *Clostridium botulinum* is suspended in a quantity of seed-medium and incubated at 34±1° C. for 24–48 hours in an anaerobic environment. Preferably, growth in stage one proceeds for approximately 48 hours. In stage two, a portion or all of the stage one medium containing *Clostridium botulinum* is used to inoculate a stage two seed medium for further growth. After inoculation, the stage two medium is incubated at 34±1° C. for approximately 1–4 days also in an anaerobic environment. Preferably, growth in the stage two seed medium proceeds for approximately 3 days. It is also preferable that growth in seed media in any stage does not result in cell lysis before inoculation of fermentation media with the final growth in seed medium.

Standard fermentation media containing animal by-products for the growth of *Clostridium botulinum* can be based on a recipe of Mueller and Miller (MM; J. Bacteriol. 67:271, 1954). The ingredients in MM media containing animal by-products include BHI and NZ-CaseTT. NZ-CaseTT is a commercially available source of peptides and amino acids which are derived from the enzymatic digestion of caseins, a group of proteins found in animal milk. The present invention demonstrates that non-animal based products may be substituted for BHI and NZ-CaseTT in fermentation media. For example but without limitation, soy-based products can replace the animal-based components of MM media used for fermentation of *Clostridium botulinum*. Preferably, the soy-based products are water-soluble and derived from hydrolyzed soy, although as previously discussed, insoluble soy products can also be used to practice the present invention.

Any source of soy-based products may be used in accordance with the present invention. Preferably, the hydrolyzed soy is obtained from Quest International (Sheffield) under the tradename, Hy-Soy or from DMV International Nutritionals (Fraser, N.Y.) under the tradename, SE50MK. Soluble soy products can be also obtained from a variety of sources including but not limited to Soy peptone (Gibco) Bac-soytone (Difco), AMISOY (Quest), NZ soy (Quest), NZ soy BL4, NZ soy BL7, and SE50MK (DMV International Nutritionals, Fraser, N.Y.).

In another preferred embodiment of the present invention, the medium used for fermentation of *Clostridium botulinum* is free of animal by-products and comprises hydrolyzed soy, glucose, NaCl, $Na_2HPO_4$, $MgSO_4 7H_2O$, $KH_2PO_4$, L-cysteine, L-tyrosine, and powdered iron. As disclosed for the seed medium, hydrolyzed soy can replace animal by-products in fermentation medium. These animal by-products include BHI and NZ-CaseTT (enzymatically digested casein).

The concentration of Hy-Soy in the fermentation medium for production of *botulinum* toxin preferably ranges between approximately 10–100 g/L. Preferably, the concentration of Hy-Soy ranges between approximately 20–60 g/L. Most preferably, the concentration of Hy-Soy in the fermentation medium is approximately 35 g/L. For maximal production of *botulinum* toxin, particularly preferred concentrations of components in the fermentation medium are approximately 7.5 g/L, glucose; 5.0 g/L NaCl; 0.5 g/L $Na_2HPO_4$; 175 mg/L $KH_2PO_4$; 50 mg/L $MgSO_4 7H_2O$; 125 mg/L L-cysteine;. and 125 mg/L L-tyrosine. The amount of powdered iron used can range from 50 mg/L to 2000 mg/L. Preferably, the amount of powdered iron ranges between approximately. 100 mg/L and 1000 mg/L. Most preferably, the amount of powdered iron used in fermentation media ranges between approximately 200 mg/L and 600 mg/L.

For optimal levels of toxin production, the initial pH (before autoclaving) of the soy-based fermentation media ranges preferably between approximately 5.5 to 7.1. Preferably the initial pH of the fermentation medium is between approximately 6.0 to 6.2. As described for the seed medium, the components of the fermentation medium, including glucose and iron, are preferably autoclaved together for sterilization.

Preferably, a portion of the second stage seed medium used for growth of *Clostridium botulinum* is used to inoculate the fermentation medium. Fermentation occurs in an anaerobic chamber at approximately 34±1° C. for approximately 7 to 9 days. Growth is monitored by measuring the optical density (O.D.) of the medium. Fermentation preferably is stopped after cell lysis has proceeded for at least 48 hours as determined by growth measurement (optical density). As cells lyse, the O.D. of the medium will decrease.

In a preferred embodiment of the present invention, cultures of *Clostridium botulinum* used for long-term storage of *Clostridium botulinum* and inoculation of the seed medium are grown and lyophilized in soy-milk prior to storage at 4° C. Cultures of *Clostridium botulinum* in animal milk lyophilized for storage can also be used for the production of *botulinum* toxin. However, to maintain media that are substantially free of animal by-products throughout the production of *botulinum* toxin, it is preferred that the initial culture of *Clostridium botulinum* be preserved in soy milk and not animal milk.

EXAMPLES

The following examples set forth specific methods encompassed by the present invention and are not intended to limit the scope of the invention. *Clostridium botulinum* cultures can be obtained from several sources, including List Laboratories, Campbell, Calif. All experiments and media can be prepared with double-distilled water. In all the Examples below "*Clostridium botulinum*" means the Hall A (ATCC designation number 3502) strain of *Clostridium botulinum* type A.

Example 1

Preparation of an Animal Product Free Seed Medium for *Clostridium Botulinum*

A control seed medium can be prepared using the following ingredients for each one 1 liter of medium: NaCl (5 g), Bacto-peptone (10 g), glucose (10 g), BHI (to 1 liter), pH 8.1 (adjusted with 5 N NaOH).

A test (animal product free) seed medium can be prepared using the following ingredients for each one 1 liter of medium: NaCl (5 g), Soy-peptone (10 g), glucose (10 g), Hy-Soy (35 g/liter, to make up 1 liter of media fluid), pH 8.1 (adjusted with 5 N NaOH).

Example 2

Culturing *Clostridium Botulinum* in an Animal Product Free Seed Medium

A lyophilized culture of the *Clostridium botulinum* can be suspended in 1 ml of each of the control and test seed medium of Example 1, divided (each seed media) into two tubes of which each can contain 10 ml of the respective seed media, and then incubated at 34° C. for about 24–48 hours. One ml of culture can be then used to inoculate a 125 ml DeLong Bellco Culture Flask containing 40 ml of (the respective) seed media. The inoculated culture can be incubated at 33° C. ±1° C. for 24 hours in a Coy Anaerobic Chamber (Coy Laboratory Products Inc., Grass Lake, Mich.).

Example 3

Preparation of an Animal Product Free Fermentation Media for *Clostridium Botulinum*

A basal fermentation medium can be prepared using the following ingredients for each two liters of medium glucose (15 g) NaCl (10 g), NaH$_2$PO$_4$ (1 g), KH$_2$PO$_4$ (0.350 g), MgSO$_4$7H$_2$O (0.1 g), cysteine-HC (0.250 g), tyrosine-HCl (0.250 g), powdered iron (1 g), ZnCl$_2$ (0.250 g), and MnCl$_2$ (0.4 g).

A control fermentation medium can be prepared using the following ingredients for each two liters of medium prepared: BHI (500 ml; this corresponds to about 45.5 grams of dry weight beef heart infusion), NZ-CaseTT (30 g), and basal medium (to 2 liters), pH 6.8.

The basal fermentation medium can be prepared first and it's adjusted to pH 6.8. The beef heart infusion (BHI) BHI can then be prepared and it's pH adjusted to 0.8 with 5 N NaOH. The BHI can then be added to the basal medium. Next the NZ-CaseTT can be prepared. The NZ-Case TT is then added to the to basal medium to which the beef heart infusion has already been added, and dissolved by addition of HCl. The pH can then be adjusted to 6.8 with 5 N NaOH. This medium can then be separated into 8 ml portions into each of sixteen 100 mm test tubes, following by autoclaving for 25 minutes at 120° C.

A test fermentation medium (animal product free) can be prepared by substituting a test nitrogen source for the BHI present in the control fermentation medium. Suitable test fermentation medium nitrogen sources include: Hy-Soy (Quest), AMI-Soy (Quest), NZ-Soy (Quest), NZ-Soy BL4 (Quest), NZ-Soy BL7 (Quest), Sheftone D (Sheffield), SE50M (DMV), SE50 (DMV), SE %)MK (DMV), Soy Peptone (Gibco), Bacto-Soyton (Difco), Nutrisoy 2207 (ADM), Bakes Nutrisoy (ADM) Nutrisoy flour, Soybean meal, Bacto-Yeast Extract (Difco) Yeast Extract (Gibco), Hy-Yest 412 (Quest), Hy-Yest 441 (Quest), Hy-Yest 444 (Quest), Hy-Yest (455 (Quest) Bacto-Malt Extract (Difco), Corn Steep, and Proflo (Traders).

The test fermentation-medium can be prepared as set forth above for a control fermentation medium except that BHI is excluded and the relevant nitrogen source can be first adjusted to pH 6.8 with 3 N HCl or with 5 N NaOH. The media can be allocated to in 8 ml portions to sixteen 100 mm test tubes, followed by autoclaving for 20–30 minutes at 120° C.

Example 4

Growth of *Clostridium Botulinum* in an Animal Product Free Fermentation Medium

A 40 μl portion of the test seed medium culture (animal product free) can be used to inoculate each 8 ml control or test fermentation medium aliquot in an 8 ml 16×100 mm test tube. The cultures can then be incubated at 33±1° C. for 24 hours. Tubes can then be incubated in an anaerobic chamber to allow for growth of the bacterium. Each medium assay can be performed in triplicate (i.e. can involve three independent inoculations of the same medium), and can also include a non-inoculated control which can be used as the blank for the spectrophotometer). Growth (as determined by optical density, OD) can be measured every 24 hours with a Turner Spectrophotometer (Model 330) at 660 nm. Cultivation should be stopped after cell lysis has lasted for about 48 hours and *botulinum* toxin production can then be measured.

Additional experiments can be carried out with a Hy-Soy fermentation medium containing the following ingredients for each 500 ml of the medium: Hy-Soy (17.5 g), glucose (3.75 g); NaCl (2.5 g); :$Na_2HPO_4$ (0.25 g), $MgSO_4 7H_2O$ (0.025 g), $KH_2PO_4$ (0.0875 g), L-cysteine (0.0625 g), L-tyrosine (0.0625 g), powdered iron (0.25 g), pH 6.8.

Example 5

Determination of Botulinum Toxin Production by *Clostridium Botulinum* Grown in an Animal Product Free Fermentation Medium The cultured cells of Example 4 can be centrifuged, and the pH of the supernatant then determined. The levels of *botulinum* toxin in a given sample can be measured by adding a standard antitoxin and measuring the elapsed time before flocculation. Both Kf (the time required for flocculation to occur, in minutes) and Lf (the limit of flocculation; equivalent to 1 international unit of standard antitoxin, as established by flocculation) can be determined. 4 ml of fermentation broth can be taken from each fermentation tube for a given culture, and can be combined together so that 12 ml total can be mixed in a 15 ml centrifuge tube. The tubes can be centrifuged at 5000 rpm (3400 g) for 30 min at 4° C. 1 ml aliquots of supernatant can be added to tubes containing 0.1–0.6 ml of standard *botulinum* toxin antiserum, and the tubes can be carefully shaken to mix their contents. The tubes can then be placed in a water bath at 45±1° C. and the initial time can be recorded. The tubes can be checked frequently, and the time at which flocculation began can be recorded as Kf. The concentration of toxin in the tube in which flocculation can be first initiated can be designated LfFF. The concentration of toxin in the tube in which flocculation can be initiated second can be designated LfF.

Parallel fermentation, growth and toxin production assays can be carried out for both of: (a) the control seed medium (used to inoculate the control fermentation medium) and the control fermentation medium, to and; (2) the (animal product free), test seed medium (used to inoculate the test fermentation medium) and the (animal product free) test fermentation medium. Significantly, it can be determined that the fermentation of *Clostridium botulinum* in media free of animal products and inoculated from cultures also free of animal products (with soy-base products replacing the animal products) can result in an $Lf_{toxin}$ of approximately 50 or more. Minimally, $Lf_{toxin}$ equals approximately 10. Preferably the $Lf_{toxin}$ is at least 20. Most preferably the $Lf_{toxin}$ is greater than 50.

Additionally, it can be determined that various soy products support *Clostridium botulinum* growth in fermentation media lacking BHI. Thus soluble soy preparations can replace BHI for growth of *Clostridium botulinum*. The best concentration can be 12.5 or 25 g/L. Hy-Soy (Sheffield) can give the highest growth. Insoluble soy preparations can be less effective.

Furthermore, results can be obtained to show that Quest Hy-Soy, DMV SE50MK, and Quest NZ-Soy can be effective soy products in terms of their ability to replace BHI for *Clostridium botulinum* growth. The results can reveal that the soy products (such as Quest Hy-Soy, DMV SE50MK, and Quest NZ-Soy) that may be optimal for growth can also be effective at replacing BHI for toxin production. The best soy product for toxin production can be Quest Hy-Soy at 22.75 g/l. Higher concentrations of this product may produce better growth but not improve toxin production. Similar results can, it is proposed, be obtained with SE50MK, for which a higher concentration may generate increased growth, but not increase toxin production. NZ-Soy, on the other hand, may give higher growth and higher toxin production at its higher concentration.

Finally, it can be determined that soy products can effectively replace BHI as well as the NZ-CaseTT. Removal of NZ-CaseTT from soy-based media can reduce growth of about 2–4 fold. The best soy product for growth both in the presence and the absence of NZ-CaseTT can be SE50MK. HY-Soy can replace both BHI and NZ-CaseTT for toxin production. However, a longer fermentation cycle of 1 or 2 days may be necessary. HY-Soy could replace both BHI and NZ-CaseTT in media for toxin production. However, it can be determined that yeast extracts can be inhibitory to toxin production.

It can be determined that HY-Soy at 22.75 g/l may completely replace both BHI and HY-CaseTT for-toxin production. Unlike the effect on growth where 56.88 g/l HY-Soy can be best, 34.13 g/l HY-Soy can be best for the toxin production phase.

Thus, I have surprisingly determined if Hy-Soy or [Hy-Soy+Hy-Yest] can replace BHI and Bacto-peptone in media for seed growth of *Clostridium botulinum*. In addition, experiments can be designed to determine the optimum concentrations of components in seed media to produce the maximum levels of *botulinum* toxin production by the clostridium botulinum. Toxin production by *Clostridium botulinum* grown in seed medium and fermentation medium that is free of BHI and NZ-CaseTT can reach or exceed levels attained in media containing BHI and NZ-CaseTT.

It can be determined that the optimum concentrations of Hy-Soy or [Hy-Soy+Hy-Yest] for growth in the seed medium. Experiments can confirm that Hy-Soy can replace BHI and Bacto-peptone as the nitrogen source in seed medium for growth of *Clostridium botulinum* and for production of Botulinum Toxin in the subsequent fermentation phase. Also, Hy-Soy as nitrogen source in the seed medium, as compared to Hy-Soy plus Hy-Yest, can produce higher levels of Botulinum Toxin in the subsequent fermentation step. The concentrations of Hy-Soy in seed medium that produce the best levels of toxin range from approximately 62.5 g/L to 100 g/L.

Additional experiments designed to determine the optimum concentrations of Hy-Soy in the seed medium for the maximum production of *botulinum* toxin by *Clostridium botulinum* by fermentation. Thus, 30 g, 50 g, 75 g and 100 g of Hy-Soy in the seed medium can all resulted in production of *botulinum* toxin by fermentation of *Clostridium botulinum* and this is comparable or exceeds levels of *botulinum* toxin made in seed medium containing BHI and Bacto-peptone as a nitrogen source.

It can be found that a concentration of 100 g/L Hy-Soy in the seed medium resulted in the highest levels of toxin production in the subsequent fermentation step. In addition, the data indicate that seed step-1 of Hy-Soy seed medium produced greater growth after 48 hours than after 24 hours.

Various publications, patents and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of animal product free processes are within the scope of the present invention.

Accordingly, the spirit and scope of the following claims should not be limited to the descriptions of the preferred embodiments set forth above.

I claim:

1. A method for production of a *botulinum* toxin, the method comprising the steps of:
   (a) providing a first medium that is no more that 1% by weight of an animal based product and that comprises a protein product of soybean;
   (b) culturing a *Clostridium botulinum* bacterium in the first medium under conditions that permit growth of the *Clostridium botulinum* bacterium;
   (c) providing a second medium that is no more than 1% by weight of an animal based product and that comprises a protein product of soybean;
   (d) inoculating the second medium with the first medium;
   (e) culturing the *Clostridium botulinum* bacterium in the second medium under conditions that allow production of a *botulinum* toxin; and
   (f) recovering the *botulinum* toxin.

2. The method of claim 1, wherein in the step of providing a first medium, the first medium comprises a hydrolyzed soy, and wherein in the step of inoculating a second medium, the second medium comprises a hydrolyzed soy.

3. The method of claim 1, wherein in the step of culturing a *Clostridium botulinum* in a first medium, the conditions comprise a temperature of about 34 degrees Celsius, and further comprise no decrease in cell density during culturing,
   wherein In the step of inoculating a second medium with a first medium, 2 to 4 percent of the first medium is used to inoculate the second medium, and wherein in the step of culturing the bacterium in the second medium, the conditions that allow growth comprise a temperature of approximately 34 degrees Celsius and further comprise culturing until cell density of the culture decreases due to cell lysis.

4. The method of claim 1, wherein the *botulinum* toxin is selected from the group consisting of *botulinum* toxins types A, B, C, D, E, F and G.

5. The method of claim 1, wherein the *botulinum* toxin is *botulinum* toxin type A.

6. The method of claim 1, wherein the *botulinum* toxin is further purified.

7. A method for production of a *botulinum* toxin type A, the method comprising the steps of:
   (a) providing a first medium that is no more that 1% by weight of an animal based product and that comprises a protein product of soybean;
   (b) culturing a *Clostridium botulinum* type A bacterium in the first medium under conditions that permit growth of the *Clostridium botulinum* bacterium;
   (c) providing a second medium that is no more than 1% by weight of an animal based product and that comprises a protein product of soybean;
   (d) inoculating the second medium with the first medium;
   (e) culturing the *Clostridium botulinum* bacterium in the second medium under conditions that allow production of a *botulinum* toxin type A; and
   (f) recovering the *botulinum* toxin type A.

8. The method of claim 7, wherein the protein product of soybean is a hydrolyzed soy.

9. A method for production of a *botulinum* toxin type A, the method comprising the steps of:
   (a) providing a first medium that is no more that 1% by weight of an animal based product and that comprises a hydrolyzed soy;
   (b) culturing a *Clostridium botulinum* type A bacterium in the first medium under conditions that permit growth of the *Clostridium botulinum* bacterium;
   (c) providing a second medium that is no more than 1% by weight of an animal based product and that comprises a hydrolyzed soy;
   (d) inoculating the second medium with the first medium;
   (e) culturing a the *Clostridium botulinum* bacterium in the second medium under conditions that allow production of a *botulinum* toxin type As; and
   (f) recovering the *botulinum* toxin type A.

* * * * *